United States Patent

Cewers

[11] Patent Number: 6,003,836
[45] Date of Patent: Dec. 21, 1999

[54] VALVE

[75] Inventor: Göran Cewers, Lund, Sweden

[73] Assignee: Siemens Elema AB, Solna, Sweden

[21] Appl. No.: 08/804,383

[22] Filed: Feb. 21, 1997

[30] Foreign Application Priority Data

Mar. 8, 1996 [SE] Sweden .................................. 9600913

[51] Int. Cl.⁶ .................................................. F16K 31/02
[52] U.S. Cl. ..................................... 251/129.06; 251/129.2
[58] Field of Search ........................ 251/129.06, 129.01, 251/129.2; 137/82

[56] References Cited

U.S. PATENT DOCUMENTS

| | | | |
|---|---|---|---|
| 2,824,292 | 2/1958 | Christoph | 137/82 X |
| 2,950,728 | 8/1960 | Watrous | 137/82 |
| 3,174,716 | 3/1965 | Salter | 251/129.06 |
| 3,614,486 | 10/1971 | Smiley | 251/129.06 X |
| 4,610,426 | 9/1986 | Brandner | 251/129.06 |
| 5,265,594 | 11/1993 | Olsson et al. | |
| 5,381,817 | 1/1995 | Gassman et al. | 137/82 |
| 5,628,411 | 5/1997 | Mills et al. | 251/129.06 |

FOREIGN PATENT DOCUMENTS 0 046 431   2/1982   European Pat. Off. .

*Primary Examiner*—John Rivell
*Attorney, Agent, or Firm*—Hill & Simpson

[57] ABSTRACT

A valve for regulating a gas or liquid has a valve housing with an inlet and an outlet. A valve seat is arranged in the valve housing and connects the inlet to the outlet via a valve opening. A valve body facing the valve seat is formed by a band attached at a first fixation point and a second fixation point. The first fixation point is at one end of a lever. An actuator is arranged on the other end of the lever to act on the lever so the distance between the first fixation point and the second fixation point increases. The band is then stretched, and the valve opening is exposed, enabling gas/liquid to flow toward the outlet. When the actuator's action on the lever is regulated, an exact flow of gas/liquid can be regulated.

20 Claims, 2 Drawing Sheets

VALVE

BACKGROUND OF THE INVENTION

1. Field of the Invention

The present invention relates to a valve for regulating a fluid flow of the type having a valve housing with an inlet for the fluid to be regulated, an outlet for a regulated flow of fluid, a valve seat with a valve opening arranged in the valve housing and a valve body, movably arranged against the valve seat, for regulating the flow of fluid through the valve opening.

2. Description of the Prior Art

The term "fluid" as used herein refers to both liquids and gases. When the regulation of gas is described, the same description also applies to regulation of liquid, and vice-versa.

A valve is described in U.S. Pat. No. 5,265,594 having a gas inlet which opens onto a valve seat in a valve housing. A membrane and a piston are arranged at the valve seat to interact in regulating the flow of gas through the valve seat. The piston is spring-loaded, causing the membrane to press against the valve seat. A solenoid coil is arranged around the piston. When the solenoid coil is activated, the piston is electromagnetically forced against its spring-loading, and the membrane is pushed away from the valve seat by the gas in the inlet and a flow of gas then streams through the valve opening to an outlet for regulated gas. This known valve displays very good dynamics and is capable of regulating flows ranging from a few ml/s to a number of liters/s, with great accuracy. It also has a very fast response time and can change from regulation of small flows (ml/s) to regulation of large flows (lls) in only a few tenths of a second. The known valve can also regulate a flow of liquid in the corresponding manner.

These properties make this known valve particularly suitable for use in e.g. medical equipment such as ventilators and respirators. As a result of its extensive dynamics, a ventilator equipped with this known valve can be used for the treatment of both premature babies and adults. The rapid response time means that the ventilator is also able to respond very rapidly to spontaneous breathing. A patient under treatment on the ventilator never needs to feel any great resistance to breathing, something which otherwise occurs with valves lacking the same response time. A patient who e.g. takes a deep breath may require a change in flow from zero to a number of liters/s, in an initial phase of inspiration. The known valve is used e.g. in the Servo Ventilator 300, Siemens-Elema AB, Solna, Sweden Since the known valve has a relatively complex structure, it occupies a relatively large amount of space in a ventilator, is relatively expensive to manufacture and consumes a relatively large amount of energy in operation. For these reasons, this known valve is not particularly suitable for use in e.g. small, portable, battery-powered ventilators. Thus there is a need for a smaller, less energy-consuming valve whose performance is at least on a par with that of the known valve. Such a valve, preferably, should also be simpler and, accordingly, less expensive to manufacture without sacrificing valve reliability.

SUMMARY OF THE INVENTION

A valve having the attributes described immediately above is achieved in accordance with the invention having a first fixation point and a second fixation point arranged in the valve housing, at least one actuator is arranged to change the distance between the first fixation point and the second fixation point, and with the valve body mounted between the first fixation point and the second fixation point and devised to be deformed in its area of contact with the valve seat when the distance between the first fixation point and the second fixation point is changed, the valve body's movement in relation to the valve seat being controllable with the actuator for adjusting the flow of fluid at the outlet.

The valve body is preferably devised to be deformed elastically, enabling it in the relaxed state to press against and seal the valve seat. The valve body can alternatively have an articulated construction. This construction can also be given resilient properties so the valve, in the relaxed state, does not allow any fluid to pass.

DESCRIPTION OF THE PREFERRED EMBODIMENTS

Figure 1:
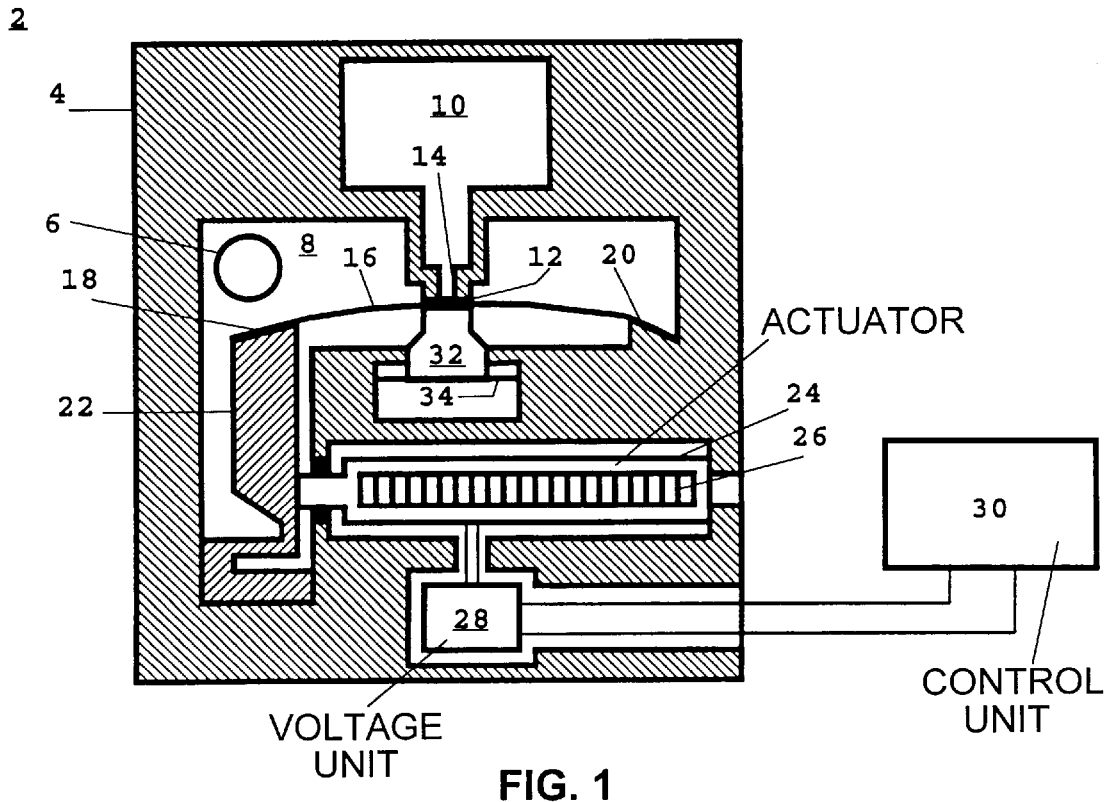
FIG. 1 shows a first embodiment of a valve according to the invention.

A first embodiment of the valve according to the invention is designated 2 and shown in FIG. 1. The valve 2 has a valve housing 4, which can be e.g. a metal block. The valve housing 4 has a gas inlet 6 for connection to some form of pressurized gas source, such as a permanent wall system. The valve housing 4 also has a cavity 8 to hold other components.

An outlet 10 for regulated gas is part of the valve housing 4. The outlet 10 can be connected to a tubing system or the equivalent, especially when the valve 2 is used in a ventilator or the like.

In this embodiment, a valve seat 12 is provided as part of the valve housing 4, and a valve opening 14 is arranged in the valve seat 12. A valve body, in the form of a band 16, presses against and seals the valve seat 12. Preferably, the band 16 is flat at the contact area with the valve seat 12 to improve the sealing. The valve opening 14 can be circular, but may have other shapes, in particular oval or elliptical. In some instances, it can be optimal for the operation of the valve 2 if the valve opening 14 at the contact area to the band 16 has a circumference which is as large as possible in relation to the area of the opening 14.

The band 16 is attached between a first fixation point 18 and a second fixation point 20. The first fixation point 18 is at one end of a lever 22, an actuator 24 being arranged in the valve housing 4 at the other end of the lever to mechanically act on the lever 22. When the actuator 24 presses on the lever 22, the distance will increase between fixation points 18 and 20, thereby stretching the band 16 and opening a passage for gas through the valve opening 14.

The actuator 24 is a piezo stack 26, formed by a number of piezoelectric elements, to which voltage can be applied by a voltage unit 28, thereby causing the elements to expand. The voltage unit 28 can be regulated by a control unit 30. Control can be exercised in a number of known ways. For optimum performance, some form of feedback, with measurement of flow and/or pressure, should be employed. In principle, all known applicable control methods can be used.

The actuator 24, and in particular the piezo stack 26, can be completely isolated from the fluid. The actuator 24 is therefore easier to protect against erosive or corrosive fluids. When regulating explosive fluids, it is also safer for the actuator 24 (and voltage source 28) to be completely isolated from the fluid.

The design of the lever 22 and the bent band 16 ensure that there is a large mechanical gear ratio between the actuator's movement and the band's downward movement at the valve opening 14. A mechanical gear ratio in a range between 50 and 200 can be attained when the lever and band are suitably dimensioned without the mechanical mass becoming overly large. A small mechanical mass means that acceleration in the valve control is very fast, enabling the valve to display a very fast response time, i.e. only a few tenths of a millisecond.

To prevent leakage and ensure that no gas passes the valve 2 when it is closed, a shoulder 32 is arranged under the band 16 by the valve seat 12. The shoulder 32 rests on a resilient membrane 34 which presses the shoulder 32 against the valve seat 12 when the valve is unloaded. The shoulder 32 also helps damp oscillations which could otherwise disrupt regulation of gas flow. The higher gas pressure in the cavity 8 in this design also helps press the band 16 against the valve seat 12, since pressure is lower at the outlet 10. It is particularly in this instance that the shape of the opening 14 is vital. A small ratio between circumference and area enhances the closing force (beneficial when the difference in pressure is smaller) and a large ratio reduces the closing force (beneficial when the difference in pressure is higher).

The entire valve 2 has a relatively flat design. The valve housing 4 can measure about 100×100 mm with a depth of about 20 mm. Both smaller and larger valves can be devised, depending on the desired performance and fluid (gas or liquid). The outlet 10, cavity 8, inlet 6 and other compartments for the actuator 24, power source 28 and shoulder 32 can be milled from a single block of metal. In this embodiment, the lever 22 is a separate unit arranged in the cavity 8. The band 16 is appropriately made of thin, non-corroding sheet metal so it is capable of withstanding aggressive substances. The band 16 could also be made in other resistant materials having the required properties, e.g. ceramics. The lever 22 is preferably made of steel or titanium, but other materials are also possible to use.

Figure 2:
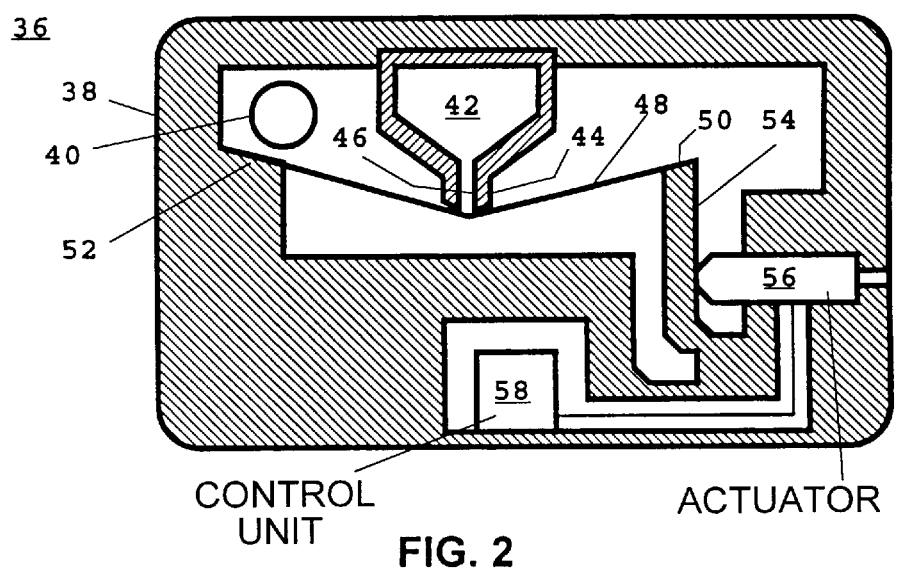
FIG. 2 shows a second embodiment of a valve according to the invention.

FIG. 2 shows a second embodiment, designated 36, of the valve according to the invention. The valve 36 has a valve housing 38 with an inlet 40 and an outlet 42. The outlet 42 is a separate component placed inside the valve housing 38. A valve seat 44 with a valve opening 46 is connected to the outlet 42. A band 48 is arranged under tension between a first fixation point 50 and a second fixation point 52. In contrast to the previous embodiment, the band 48 in this instance is triangular, and its concave side faces the valve seat 44, pressing against same when the valve 36 is closed. The first fixation point 50 is one end of a lever 54, formed as an integral part of the valve housing 38. An actuator 56, made of a magnetostrictive material, is arranged to act on the lever 54. The magnetostrictive material in the actuator 54 is regulated by a control unit 58 arranged in the valve housing 38.

The triangular shape is preferably somewhat truncated at the contact area with the valve seat 44. It could even be made to resemble half a hexagon.

In the same way as in the valve 2 in FIG. 1, the valve 36 is opened to regulate a gas or a liquid when the actuator 56 acts on the lever 54, causing the distance between the first fixation point 50 and the second fixation point 52 to decline. As a result, the concavity of the band 48 increases (the apex angle of the triangle decreases) and its midpoint is pushed away from the valve seat 44.

In principle, the band 48 could even be stretched in the unloaded state and elastically buckled by the action of the actuator 56 on the lever 54. Buckling can only be performed in one direction because of the valve seat 44. The influx of pressurized fluid could be through the outlet 42 and outflow through the inlet 40 in order to reinforce buckling. The band 48 can also be devised to facilitate buckling.

Figure 3:
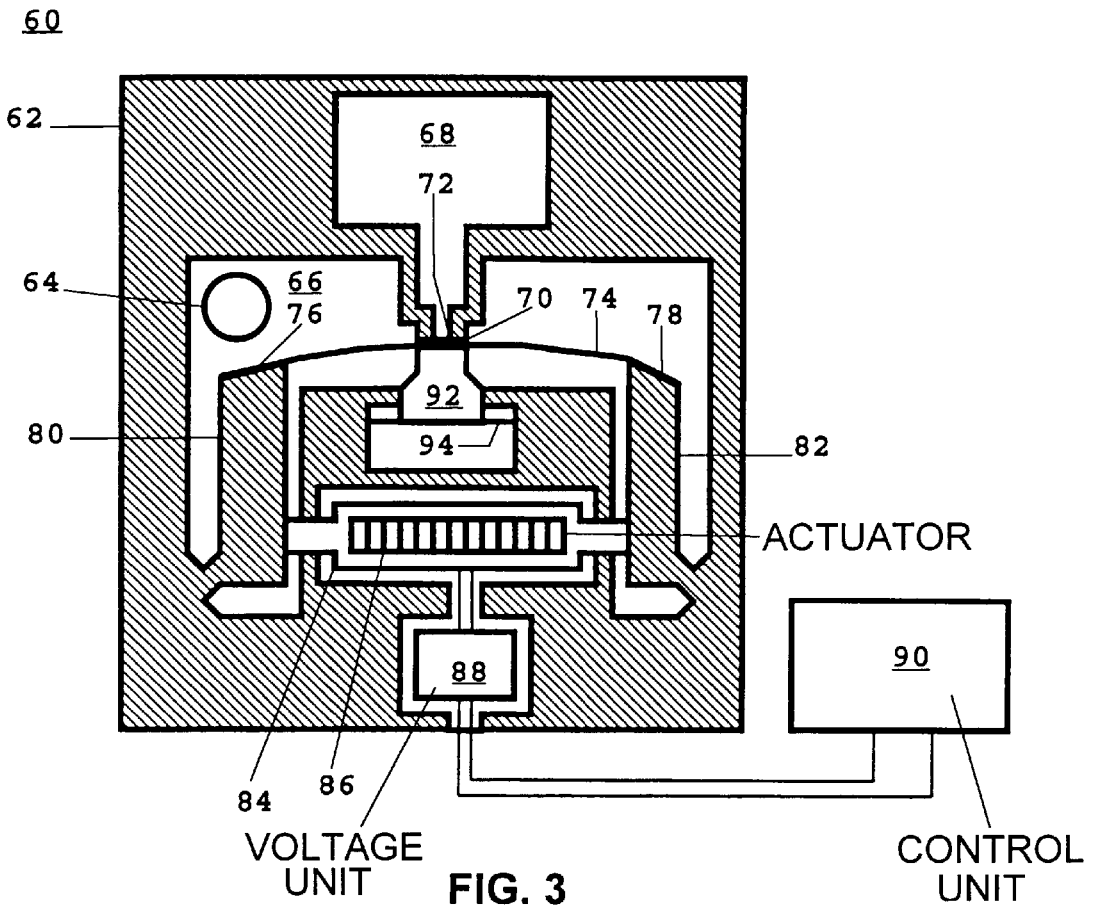
FIG. 3 shows a third embodiment of a valve according to the invention.

FIG. 3 shows a third embodiment of the valve designated 60. The valve 60 has a valve housing 62 with an inlet 64 to a cavity 66 in the valve housing 62. An outlet 68 carries regulated gas from the valve 60. A valve seat 70 is arranged in the cavity 66 and connects the cavity 66 to the outlet 68 via a valve opening 72. A band 74 is mounted under tension between a first fixation point 76 and a second fixation point 78. The band 74 is tensioned so it bulges with the convex side of the band 74 pressing against the valve opening 72 in the valve seat 70.

The first attachment point 76 is at one end of a first lever 80, and the second attachment point 78 is at one end of a second lever 82. The levers 80 and 82 are operated with an actuator 84 so the band 74 is stretched by action on the levers 80 and 82. Gas then passes from the cavity 66 through the valve opening 72 to the outlet 68. As in the first embodiment, the actuator 84 is formed by a piezo stack 86. The piezo stack 86 is regulated from a voltage unit 88 which is controlled, in turn, by a control unit 90. Two actuators can be provided, as an alternative to one actuator 84, each regulating one lever 80 or 82.

A shoulder 92 is arranged under the band 74 to damp oscillations and effectively prevent leakage through the valve 60. The shoulder 92 is suspended in a membrane 94 so it can elastically yield during regulation when the band 74 is stretched.

In contrast to the previous embodiments, most of the valve 60 in this instance is made in a single piece, i.e. the levers 80 and 82 and the valve seat 70 with the valve opening 72 and outlet 68 are all contained in a single valve housing 62. The valve housing 62 can be made e.g. from a piece of brass or the like into which the cavity 66, the inlet 64, the outlet 68 and cavities for the shoulder 92, the membrane 94, the actuator 84 and voltage unit 88 are milled or arranged in some other way. A lid 96 is connected to the valve 60, as shown in FIG. 4.

Figure 4:
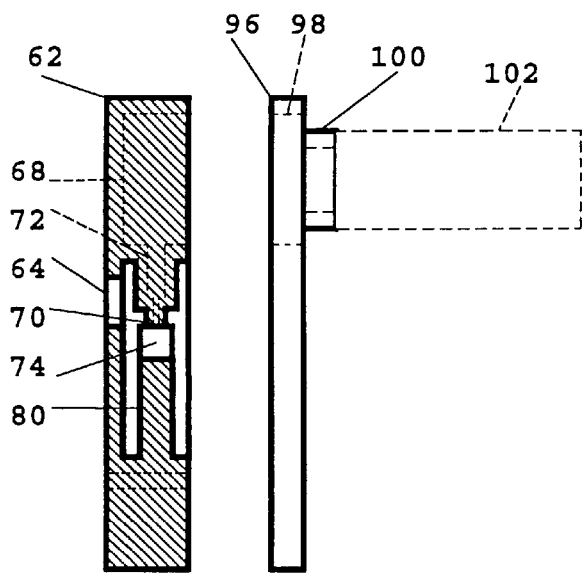
FIG. 4 shows the third embodiment from another angle.

FIG. 4 also shows how the outlet 68 is connected via a channel 98 (dashed) in the lid 96 to a connection part 100 for a tube 102 or the like. In addition, FIG. 4 shows the flat design of the valve 60.

The embodiments can be interchanged or combined, where possible, i.e. the lever 22 in the valve 2 (FIG. 1) can, in the same way as in the third embodiment (FIGS. 3, 4), be devised as an integral part of the valve housing 4. In the corresponding manner, the outlet 10 with the valve seat 12 and valve opening 14 can, as in the second embodiment (FIG. 2), be devised with separate components. The actuator 24 can be made of a magnetostrictive material, as in the second embodiment. The band can be triangular (including truncated triangles and half hexagons) in all instances or be combinations of arched and triangular shapes. The triangular shape is preferable for an array in which the distance between fixation points increases, since an effective change in the tip is achieved without losing movement (a semicircle will first assume a more triangular shape when stretched and then the "tip" will move). In a corresponding manner, other specific configurations can be interchanged in all embodiments.

Although the shown embodiments illustrate actuators which are mounted to increase in length when activated, they may also be mounted for compression. In particular piezoelectric elements can operate in such manner. Other actuators than piezo and magnetostrictive can also be use, e.g. hydraulic systems and expanding plastics.

The valves 2, 36 and 60 do not need to be devised as a flat block. The inlet and outlet can be located in other ways, e.g. so a gas or liquid is connected in the band's extension, and the outflow of gas/liquid can be returned in the same or in any direction. Incorporation and connection requirements for the valve govern the location of the inlet and outlet.

The valve seat can be selected to be soft or hard, depending on circumstance. A soft valve seat is easier to effectively seal, but requires larger movement from the valve body (and thus the actuator). A hard valve seat, on the other hand, does not require as large movement, but is more difficult to effectively seal. It should be noted that movements of half a millimeter for the valve body (band) is sufficient for a vast amount of applications. More or less movement can be achieved by proper selection of actuator, lever and band.

As already noted, regulation of the valves 2, 36 and 60 is relatively uncomplicated. The band 16, 48 or 74, with the lever 22, 54, 89 or 82, responds with such a large movement, when acted upon by the actuator 24, 56 or 84, and has such a brief response time that simple feedback from a flow meter or pressure meter (not shown in the FIG. but suitably located by the outlet) can be used with a target value for the regulated gas in order to generate an error signal which, via an operation amplifier, is able to regulate the valve 2, 36 or 60. The entire valve 2, 36 or 60 is accordingly very fast (i.e. has a short response time), accurate, energy-saving (i.e. has a low energy consumption) and compact (compared to previously known valves with corresponding performance) and displays dynamics on a par with the dynamics of the known valve. Pressure sensors can be located at both the inlet and outlet to measure the respective pressure. A conversion from the mass flow (STP) of gas to volume flow (ATP) can then be made. Atmospheric pressure could also be measured.

Although modifications and changes may be suggested by those skilled in the art, it is the intention of the inventors to embody within the patent warranted hereon all changes and modifications as reasonably and properly come within the scope of their contribution to the art.

I claim as my invention:

1. A valve for regulating a fluid flow comprising:

a valve housing having an inlet for a fluid to be regulated and an outlet for a regulated flow of said fluid;

a valve seat with a valve opening disposed in said housing;

a valve body extending between a first fixation point and a second fixation point in said housing and having an area of contact with said valve seat;

actuator means for changing a distance in said housing between said first fixation point and said second fixation point and for thereby deforming said valve body in said area of contact with said valve seat for regulating a flow of said fluid through said valve opening and thus for regulating a flow of said fluid at said outlet, including an actuator and a displaceable element, displaced by a displacement distance by said actuator, and a lever having a first end in contact with said displacement element, and a second end at which said first fixation point is disposed, said lever being mounted in said housing for causing said distance between said first fixation point and said second fixation point to change, upon actuation of said actuator, by a distance larger than said displacement distance.

2. A valve as claimed in claim 1 wherein said lever is a first lever and wherein said displaceable element is a first displaceable element, and wherein said actuator means comprises a second displaceable element, displaced by said displacement distance upon actuation of said actuator, and said valve further comprising a second lever, having a first end at which said second fixation point is disposed and a second end in contact with said second displacement element, said second lever being mounted in said housing for causing said distance between said first fixation point and said second fixation point to change by an amount larger than said displacement distance upon actuation of said actuator.

3. A valve as claimed in claim 1 wherein said valve body comprises a band having a length which is longer than said distance between said first fixation point and said second fixation point and being mounted under tension between said first fixation point and said second fixation point.

4. A valve as claimed in claim 3 wherein said band is arched between said first fixation point and said second fixation point.

5. A valve as claimed in claim 3 wherein said band is triangular.

6. A valve as claimed in claim 3 wherein said band has a concave surface, having a concavity associated therewith, facing said valve seat, and wherein said actuator means comprises means for reducing said distance between said first fixation point and said second fixation point by increasing said concavity for regulating said flow of said fluid to said outlet.

7. A valve as claimed in claim 3 wherein said band has a convex surface, having a convexity associated therewith, facing said valve seat, and wherein said actuator means comprises means for increasing said distance between said first fixation point and said second fixation point by increasing said convexity for regulating said flow of said fluid to said outlet.

8. A valve as claimed in claim 1 wherein said valve body comprises a band having a length which is longer than said distance between said first fixation point and said second fixation point and being mounted under compression between said first fixation point and said second fixation point.

9. A valve as claimed in claim 8 wherein said band is arched between said first fixation point and said second fixation point.

10. A valve as claimed in claim 8 wherein said band is triangular.

11. A valve as claimed in claim 8 wherein said band has a concave surface, having a concavity associated therewith, facing said valve seat, and wherein said actuator means comprises means for reducing said distance between said first fixation point and said second fixation point by increasing said concavity for regulating said flow of said fluid to said outlet.

12. A valve as claimed in claim 8 wherein said band has a convex surface, having a convexity associated therewith, facing said valve seat, and wherein said actuator means comprises means for increasing said distance between said first fixation point and said second fixation point by increasing said convexity for regulating said flow of said fluid to said outlet.

13. A valve as claimed in claim 1 wherein said actuator comprises a piezoelectric actuator.

14. A valve as claimed in claim 1 wherein said actuator comprises a magnetostrictive actuator.

15. A valve as claimed in claim 1 wherein said fluid has an unregulated fluid pressure associated therewith, and wherein inlet and said outlet and said valve body are disposed in said housing so that said unregulated fluid pressure forces said valve body in a closing direction toward said valve seat.

16. A valve as claimed in claim 1 wherein said inlet and said outlet and said valve opening define a fluid flow path in said housing, and said valve further comprising a seal in said housing separating said actuator means from said fluid flow path.

17. A valve as claimed in claim 1 wherein said valve opening has an optimized ratio between a circumference of said valve opening and an area of said valve opening.

18. A valve as claimed in claim 1 wherein said valve opening is circular.

19. A valve as claimed in claim 1 wherein said valve opening is oval.

20. A valve as claimed in claim 1 wherein said valve opening is elliptical.

* * * * *